US00PP27136P2

(12) United States Plant Patent
Uchneat

(10) Patent No.: US PP27,136 P2
(45) Date of Patent: Sep. 6, 2016

(54) ***IMPATIENS* PLANT NAMED 'BALBONICHER'**

(50) Latin Name: *Impatiens walleriana*
Varietal Denomination: Balbonicher

(71) Applicant: Ball Horticultural Company, West Chicago, IL (US)

(72) Inventor: Michael S. Uchneat, Bellefonte, PA (US)

(73) Assignee: Ball Horticultural Company, West Chicago, IL (US)

( * ) Notice: Subject to any disclaimer, the term of this patent is extended or adjusted under 35 U.S.C. 154(b) by 65 days.

(21) Appl. No.: 14/544,809

(22) Filed: Feb. 19, 2015

(51) Int. Cl.
*A01H 5/02* (2006.01)

(52) U.S. Cl.
USPC ..... Plt./317

(58) Field of Classification Search
USPC ..... Plt./263.1, 317
See application file for complete search history.

*Primary Examiner* — Susan McCormick Ewoldt
*Assistant Examiner* — Karen Redden
(74) *Attorney, Agent, or Firm* — Audrey Charles

(57) ABSTRACT

A new and distinct cultivar of *Impatiens* plant named 'Balbonicher', characterized by its double-type, medium red-colored flowers, dark green-colored foliage, and moderately vigorous, compact-mounded growth habit, is disclosed.

1 Drawing Sheet

Latin name of genus and species of plant claimed: *Impatiens walleriana.*
Variety denomination: 'Balbonicher'.

BACKGROUND OF THE INVENTION

The present invention relates to a new and distinct cultivar of *Impatiens* plant botanically known as *Impatiens walleriana* and hereinafter referred to by the cultivar name 'Balbonicher'.

The new cultivar originated in a controlled breeding program in Bellefonte, Pa. during April 2009. The objective of the breeding program was the development of *Impatiens* cultivars with fully double-type, large flowers, and with a compact-mounded growth habit.

The new *Impatiens* cultivar is the result of cross-pollination. The female (seed) parent of the new cultivar is the proprietary *Impatiens walleriana* breeding selection coded 5446c-1, not patented, characterized by its semi-double type, light red-colored flowers, medium green-colored foliage, and moderately vigorous, mounded growth habit. The male (pollen) parent of the new cultivar is the proprietary *Impatiens walleriana* breeding selection coded 5418-2, not patented, characterized by its double-type, dark red-colored flowers, medium green-colored foliage, and moderately vigorous, spreading growth habit. The new cultivar was discovered and selected as an individual flowering plant within the progeny of the above stated cross-pollination during March 2010 in a controlled environment in Bellefonte, Pa.

Asexual reproduction of the new cultivar by terminal stem cuttings since March 2010 in Bellefonte, Pa.; Arroyo Grande, Calif.; and West Chicago, Ill. has demonstrated that the new cultivar reproduces true to type with all of the characteristics, as herein described, firmly fixed and retained through successive generations of such asexual propagation.

SUMMARY OF THE INVENTION

The following characteristics of the new cultivar have been repeatedly observed and can be used to distinguish 'Balbonicher' as a new and distinct cultivar of *Impatiens* plant:

1. Double-type, medium red-colored flowers;
2. Dark green-colored foliage; and
3. Moderately vigorous, compact-mounded growth habit.

Plants of the new cultivar differ from plants of the female parent primarily in flower form and flower color shade. Plants of the new cultivar differ from plants of the male parent primarily in growth habit. In addition, plants of the new cultivar have darker green-colored foliage than both the female and male parents.

Of the many commercially available *Impatiens* cultivars, the most similar in comparison to the new cultivar is Fiesta Ole Cherry 'Balolecher', U.S. Plant Pat. No. 13,668. However, in side by side comparisons, plants of the new cultivar differ from plants of 'Balolecher' in at least the following characteristics:

1. Plants of the new cultivar have a flower color different from plants of 'Balolecher';
2. Plants of the new cultivar have larger flowers, as measured by width and depth, than plants of 'Balolecher'; and
3. Plants of the new cultivar have larger leaves, as measured by length and width, than plants of 'Balolecher'.

BRIEF DESCRIPTION OF THE PHOTOGRAPHS

The accompanying photographs show, as nearly true as it is reasonably possible to make the same in color illustrations of this type, typical flower and foliage characteristics of the new cultivar. Colors in the photographs may differ slightly from the color values cited in the detailed description, which accurately describes the colors of 'Balbonicher'. The plants were grown in 4-inch pots for 6 weeks in a greenhouse in West Chicago, Ill.

DETAILED BOTANICAL DESCRIPTION

Figure 1:
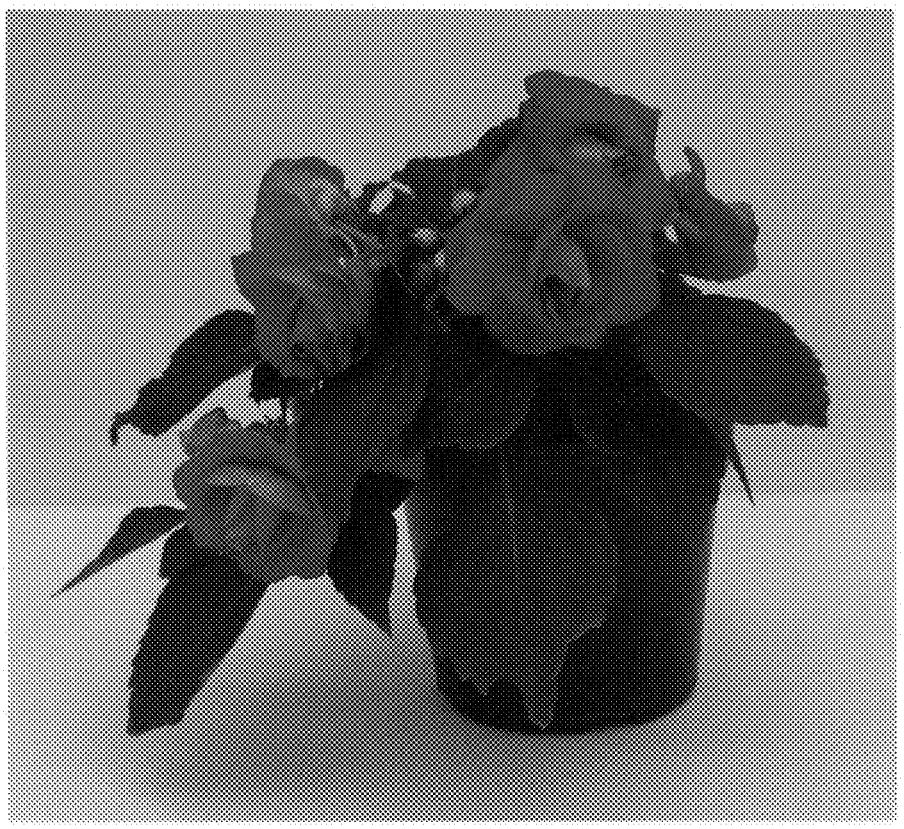
FIG. 1 illustrates a side view of the overall growth and flowering habit of 'Balbonicher'.
Figure 2:
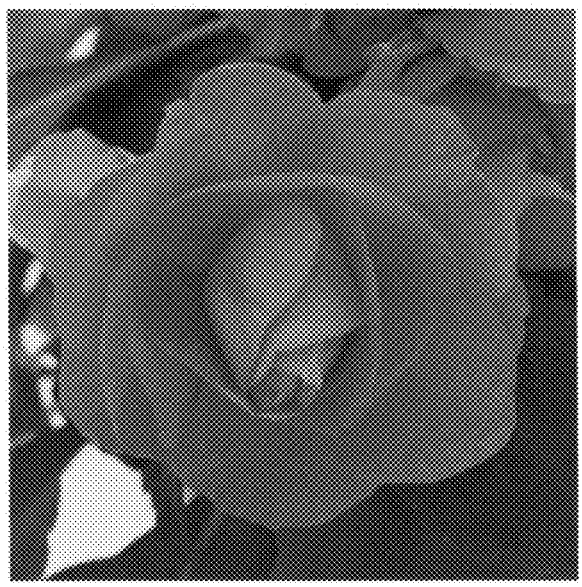
FIG. 2 illustrates a close-up view of an individual flower of 'Balbonicher'.

The new cultivar has not been observed under all possible environmental conditions to date. Accordingly, it is possible that the phenotype may vary somewhat with variations in the environment, such as temperature, light intensity, and day length, without, however, any variance in genotype.

The chart used in the identification of colors described herein is The R.H.S. Colour Chart of The Royal Horticultural Society, London, England, 2007 edition, except where general color terms of ordinary significance are used. The color values were determined in November 2014 under natural light conditions in West Chicago, Ill.

The following descriptions and measurements describe plants produced from cuttings from stock plants and grown in a glass-covered greenhouse under conditions comparable to those used in commercial practice. The plants were grown in West Chicago, Ill. in 4-inch pots for 6 weeks utilizing a soilless growth medium. Greenhouse temperatures were maintained at approximately 70° F. to 77° F. (21° C. to 25° C.) during the day and approximately 65° F. to 68° F. (18° C. to 20° C.) during the night. Greenhouse light levels of 2,500 footcandles to 6,000 footcandles were maintained during the day. Measurements and numerical values represent averages of typical plants.

Botanical classification: *Impatiens walleriana* cultivar Balbonicher.

Parentage:

*Female parent*.—Proprietary *Impatiens walleriana* breeding selection coded 5446c-1, not patented.

*Male parent*.—Proprietary *Impatiens walleriana* breeding selection coded 5418-2, not patented.

Propagation:

*Type cutting*.—Terminal stem.

*Time to initiate roots*.—Approximately 5 to 8 days.

*Time to produce a rooted cutting*.—Approximately 14 to 21 days.

*Root description*.—Fibrous.

*Rooting habit*.—Freely branching.

Plant description:

*Commercial crop time*.—Approximately 5 to 7 weeks from a rooted cutting to finish in a 10 cm pot.

*Growth habit and general appearance*.—Moderately vigorous, compact-mounded growth habit.

*Size*.—Height from soil level to top of plant plane: Approximately 10.5 cm. Width: Approximately 18.5 cm.

*Branching habit*.—Freely branching. Quantity of main branches per plant: Approximately 4.

*Branch*.—Strength: Moderately strong. Length: Approximately 5.0 cm. Diameter at central internode: Approximately 4.0 mm. Length of central internode: Approximately 1.1 cm. Texture: Glabrous. Color of young and mature stems: 146D with streaks of 187B; streaks wider at the node regions.

Foliage description:

*General description*.—Quantity of leaves per main branch: Approximately 8. Fragrance: None. Form: Simple. Arrangement: Alternate.

*Leaves*.—Aspect: Acute angle to stem, becoming perpendicular with age. Shape: Elliptic to broadly elliptic. Margin: Crenate, ciliate. Apex: Acute. Base: Attenuate. Venation pattern: Pinnate. Length of mature leaf at center of stem: Approximately 6.5 cm. Width of mature leaf at center of stem: Approximately 4.1 cm. Texture of upper surface: Sparsely pubescent. Texture of lower surface: Glabrous. Color of upper surface of young foliage: Closest to 139A with venation of 137B. Color of lower surface of young and mature foliage: Closest to 138B with irregular areas of 187B and venation of 138A. Color of upper surface of mature foliage: Closest to 137A mixed with 139A, venation of 137B.

*Petiole*.—Length: Approximately 3.0 cm. Diameter: Approximately 3.0 mm. Texture: Glabrous. Color: 147D with faint streaks of 187B.

Flowering description:

*Flowering habit*.—'Balbonicher' is freely flowering under outdoor growing conditions with substantially continuous blooming from spring through autumn and year-round in greenhouse environment.

*Lastingness of individual flower on the plant*.—Approximately 6 to 7 days.

Flower description:

*General description*.—Type: Double. Quantity per plant: Approximately 7. Fragrance: None.

*Bud*.—Rate of opening: Generally takes 2 to 3 days for bud to progress from first color to fully open flower. Quantity showing color per plant: Approximately 10.

*Bud just before opening*.—Shape: Ovoid. Length: Approximately 1.2 cm. Diameter: Approximately 1.0 cm. Color: 36B.

*Corolla*.—Shape: Hemispherical. Width: Approximately 5.1 cm. Depth: Approximately 3.2 cm. Borne: Above and below the foliage.

*Petals*.—Quantity: 55. Shape: Obovate; innermost ovate. Aspect: Flat. Appearance: Iridescent. Margin: Entire. Apex: Obtuse. Base: Attenuate. Length of outermost petals: Approximately 2.4 cm. Width of outermost petals: Approximately 2.3 cm. Length of innermost petals: Approximately 2.0 mm. Width of innermost petals: Approximately 2.0 mm. Texture of upper and lower surfaces: Glabrous. Color of upper surface when first and fully open: 45B to 45C. Color of lower surface when first and fully open: 37A with outermost having central stripe of NN155D.

*Spur*.—Quantity: 1 per flower. Length: Approximately 3.5 cm. Diameter at proximal end: Approximately 2.0 mm. Diameter at distal end: Less than 1.0 mm. Texture: Glabrous. Color: 145C with an overlay of 187C at tip.

*Peduncle*.—Strength: Moderate. Aspect: Acute angle to stem. Length: Approximately 3.8 cm. Diameter: Approximately 2.0 mm. Texture: Glabrous. Color: 146D.

*Sepals*.—Quantity per flower: 4, with one fused to base of upper petal, lower sepal typically not observed on fully-opened flower. Shape of lateral sepals: Lanceolate. Shape of lower sepal: Ovate. Apex of all sepals: Acute. Length of lateral sepals: Approximately 3.0 mm. Width of lateral sepals: Approximately 1.0 mm. Length of lower sepal: Approximately 1.3 cm. Width of lower sepal: Approximately 1.0 cm. Texture of upper and lower surfaces of all sepals: Glabrous, lower sepal papery. Color of upper and lower surfaces of lateral sepals: 144A. Color of upper and lower surfaces of lower sepal: Colorless.

*Reproductive organs*.—None observed.

Seed and fruit production: Neither seed nor fruit production has been observed.

Disease and pest resistance: Resistance to pathogens and pests common to *Impatiens* has not been observed.

What is claimed is:

1. A new and distinct cultivar of *Impatiens* plant named 'Balbonicher', substantially as herein illustrated and described.

* * * * *